United States Patent
Arodzero et al.

(10) Patent No.: US 9,541,510 B2
(45) Date of Patent: Jan. 10, 2017

(54) SYSTEM AND METHODS FOR MULTI-BEAM INSPECTION OF CARGO IN RELATIVE MOTION

(71) Applicant: American Science and Engineering, Inc., Billerica, MA (US)

(72) Inventors: Anatoli Arodzero, Billerica, MA (US); Martin Rommel, Lexington, MA (US)

(73) Assignee: American Science and Engineering, Inc., Billerica, MA (US)

( * ) Notice: Subject to any disclaimer, the term of this patent is extended or adjusted under 35 U.S.C. 154(b) by 296 days.

(21) Appl. No.: 13/685,835

(22) Filed: Nov. 27, 2012

(65) Prior Publication Data

US 2013/0136230 A1    May 30, 2013

Related U.S. Application Data

(60) Provisional application No. 61/564,526, filed on Nov. 29, 2011.

(51) Int. Cl.
| | |
|---|---|
| *G01N 23/10* | (2006.01) |
| *G01N 23/083* | (2006.01) |
| *G01N 23/04* | (2006.01) |
| *G01N 23/02* | (2006.01) |
| *G01V 5/00* | (2006.01) |

(52) U.S. Cl.
CPC ............ *G01N 23/046* (2013.01); *G01N 23/02* (2013.01); *G01N 23/083* (2013.01); *G01V 5/0016* (2013.01)

(58) Field of Classification Search
CPC .................................................. G01N 23/046
USPC ............................................................ 378/57
See application file for complete search history.

(56) References Cited

U.S. PATENT DOCUMENTS

| | | | |
|---|---|---|---|
| 5,757,009 A * | 5/1998 | Walstrom | 250/396 R |
| 6,088,423 A * | 7/2000 | Krug et al. | 378/57 |
| 6,895,079 B2 | 5/2005 | Birdwell et al. | 378/137 |
| 7,497,620 B2 | 3/2009 | Birdwell et al. | 378/205 |
| 2002/0097836 A1* | 7/2002 | Grodzins | 378/57 |
| 2006/0093088 A1 | 5/2006 | Sowerby et al. | 378/63 |
| 2007/0009081 A1 | 1/2007 | Zhou et al. | 378/10 |
| 2008/0122390 A1 | 5/2008 | Lidestri | 315/501 |
| 2009/0086907 A1* | 4/2009 | Smith | 378/57 |
| 2011/0064197 A1 | 3/2011 | Harding et al. | 378/70 |
| 2011/0206179 A1* | 8/2011 | Bendahan | G01V 5/0016 378/19 |

FOREIGN PATENT DOCUMENTS

WO    WO 99/09398 A1    2/1999    ............ G01N 23/04

OTHER PUBLICATIONS

Arke et al., 'A Solid-State Nanosecond Beam Kicker Modulator Based on the DSRD Switch,' Aug. 2011, Conf. Proc. C11-03-28.*

(Continued)

*Primary Examiner* — Robert Kim
*Assistant Examiner* — Eliza Osenbaugh-Stewar
(74) *Attorney, Agent, or Firm* — Sunstein Kann Murphy & Timbers LLP

(57) ABSTRACT

X-ray inspection of moving cargo based on acquiring multiple image lines at one time or substantially at one time. An X-ray source with multiple-beam electron beam targets creates multiple parallel X-ray fan beams. X-ray inspection systems and methods employ such multiple-beam sources for purposes of inspecting fast moving cargo.

9 Claims, 7 Drawing Sheets

(56) References Cited

OTHER PUBLICATIONS

Jin Ho Park, Authorized officer Korean Intellectual Property Office, International Search Report and Written Opinion of the International Searching Authority—International Application No. PCT/US2012/066612, dated Feb. 27, 2013 (12 pages).

* cited by examiner

SYSTEM AND METHODS FOR MULTI-BEAM INSPECTION OF CARGO IN RELATIVE MOTION

The present application claims priority from U.S. Provisional Patent Application Ser. No. 61/564,526, filed Nov. 29, 2011, and incorporated herein by reference.

TECHNICAL FIELD

The present invention relates to methods and apparatus for cargo inspection with penetrating radiation, and, more particularly, to high speed, high throughput inspection systems employing pulsed X-ray sources and providing enhanced material discrimination.

BACKGROUND ART

X-ray cargo inspection systems typically use an X-ray fan beam generated by a pulsed high-energy X-ray source, such as a linear accelerator (linac) or a betatron. The highest available pulse rates from these sources limit the line frequency of the imaging system and thus the maximum scan speed for a given line resolution. Linear accelerators are available with pulse rates up to 1000 pulses per second (pps). At that rate an object with a speed of 60 km/h moves 16.7 mm per pulse. In order to achieve a typical 4 mm vertical line pair resolution, four image lines must to be acquired simultaneously. Employing multiple sources with multiple detector arrays, however, is a costly proposition.

FIG. 1 depicts a cargo inspection system employing an x-ray transmission technique. A fan-shaped beam 12 of penetrating radiation, emitted by a source 14, is detected by elements of a detector array 16 distal to a target object, here truck 10, in order to produce images of the target object. Particular contents of the object may be discriminated and characterized on the basis of the transmission of penetrating radiation through the object and its detection by detector array 16 and its individual detector modules 18. (As used herein, the term "detector module" refers to a detector element in conjunction with its associated preprocessing electronics.) Signals from each of the detector modules, suitably pre-processed, provide inputs to processor 19, where material characteristics are computed.

Information (such as mass absorption coefficient, effective atomic number $Z_{eff}$, electron density, etc.) regarding the material composition of the contents of objects may be obtained on the basis of the interaction of X-rays with the material, and, more particularly, by illuminating the material with X-ray beams having energy spectra with more than one distinct energy endpoint (peak energy), or by employing energy discriminating detectors. Dual energy methods of material discrimination are widely used in X-ray inspection systems for security control of hand luggage in customs and other security checkpoints. Dual energy inspection is discussed in the following references, for example, which are incorporated herein by reference:

U.S. Pat. No. 5,524,133, Neale et al., "Material Identification using X-Rays" (1996) (hereinafter, "Neale '133")

U.S. Pat. No. 7,257,188, Bjorkholm, "Dual Energy Scanning of Contents of an Object" (2005)

U.S. Pat. No. 6,069,936, Bjorkholm, "Material Discrimination using Single-Energy X-Ray Imaging System" (2000)

A multi-view x-ray inspection system is disclosed in US Published Patent Application US 2011/0206179 ("Bendahan"), incorporated herein by reference, which suggests rapidly steering a single electron beam to a sequence of x-ray radiation-producing targets, and shows an embodiment in which a beam appears to be detected by multiple parallel detector arrays, although this embodiment is not described in detail.

SUMMARY OF EMBODIMENTS OF THE INVENTION

In accordance with embodiments of the present invention, a cargo inspection system is provided that employs a plurality of fan beams of penetrating radiation, for inspecting cargo in motion relative to the cargo inspection system. The cargo inspection system has a source of a beam of accelerated electrons, at least one Bremsstrahlung target for emitting penetrating radiation upon impingement by the accelerated electrons, and a plurality of collimators for forming the emitted penetrating radiation into a plurality of substantially parallel fan beams. Additionally, the cargo inspect system has a plurality of linear detector arrays, where each linear detector array receives penetrating radiation transmitted through the cargo in a corresponding fan beam, and a processor for deriving a material characteristic of the cargo for each of a plurality of lines of sight through the cargo.

In other embodiments of the present invention, the plurality of fan beams may be parallel beams, and may be emitted in planes substantially transverse to the beam of accelerated electrons. Alternatively, the plurality of fan beams may be emitted from the at least one Bremsstrahlung target in a substantially forward direction with respect to the beam of accelerated electrons. This may be accomplished by the beam of accelerated electrons impinging upon each of a plurality of Bremsstrahlung targets at slightly different angles, or by fanning out the beam of accelerated electrons and refocusing upon each of a plurality of Bremsstrahlung targets.

In accordance with further embodiments of the present invention, the source may be configured such that the beam of accelerated electrons impinges upon a plurality of Bremsstrahlung targets either simultaneously or in sequence.

In yet further embodiments, an energy spectrum characterizing the penetrating radiation may vary as a function of time.

The system may also have a speed sensor for providing a cargo speed to the processor.

In accordance with another aspect of the present invention, a method is provided for deriving a specified characteristic of an inspected object, the method has processes including:

a. irradiating the object with a plurality of substantially parallel fan beams of penetrating radiation;

b. detecting the penetrating radiation after traversal of the inspected object with a plurality of linear detector arrays, thereby generating a detector signal; and c. processing the detector signal to derive the specified characteristic of the inspected object.

The steps of associating the plurality of detector arrays with the plurality of fan beams may be performed in an interlaced pair-wise manner.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Definitions.

As used herein and in any appended claims, the term "beam" refers to a flux of particles (including photons or other massless particles) having a predominant direction referred to as the direction of the beam. Any plane containing the direction of the beam may be referred to as a plane of the beam.

The term "multiple targets" encompasses the case of a single target which is impinged upon at distinct, non-contiguous regions, thereby generating multiple beams.

The term "image" shall refer to any multidimensional representation, whether in tangible or otherwise perceptible form, or otherwise, whereby a value of some characteristic (such as fractional transmitted intensity through a column of an inspected object traversed by an incident beam, in the case of x-ray transmission imaging) is associated with each of a plurality of locations (or, vectors in a Euclidean space, typically $\mathbb{R}^2$) corresponding to dimensional coordinates of an object in physical space, though not necessarily mapped one-to-one thereonto. An image may comprise an array of numbers in a computer memory or holographic medium. Similarly, "imaging" refers to the rendering of a stated physical characteristic in terms of one or more images.

The term "image line" refers to a one-dimensional image obtained on the basis of a linear detector array upon illumination by a fan beam.

The term "concurrent X-ray beams," as used herein and in any appended claims, refers to multiple beams that exist within a time scale defined by the duration of a source pulse.

Advantages associated with feeding multiple detector arrays with a single source, as opposed to multiple sources, particularly in the field of x-ray inspection, may be achieved in accordance with various embodiments of the present invention.

Figure 1:
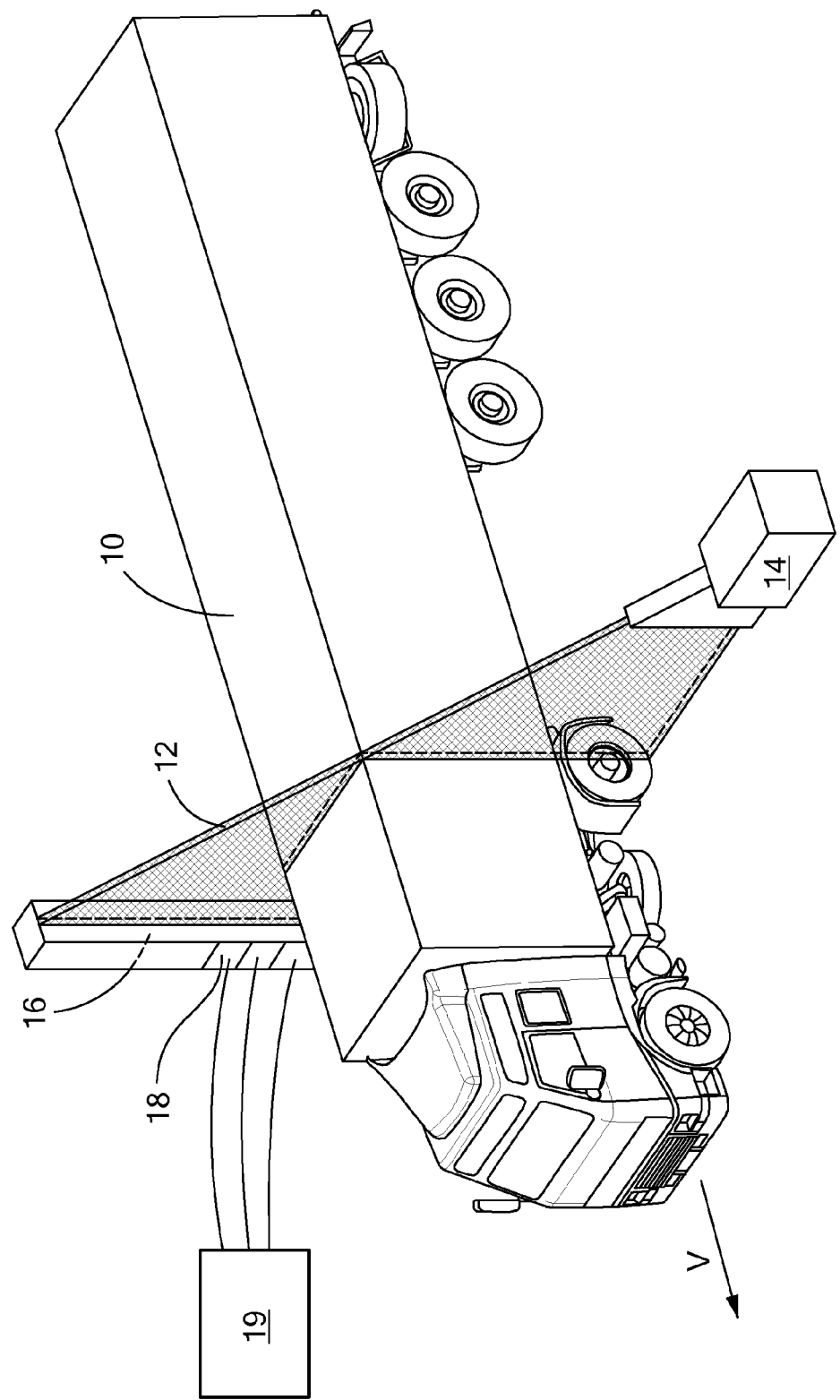
FIG. 1 is a perspective view of a prior art x-ray transmission cargo inspection system.
Figure 2:
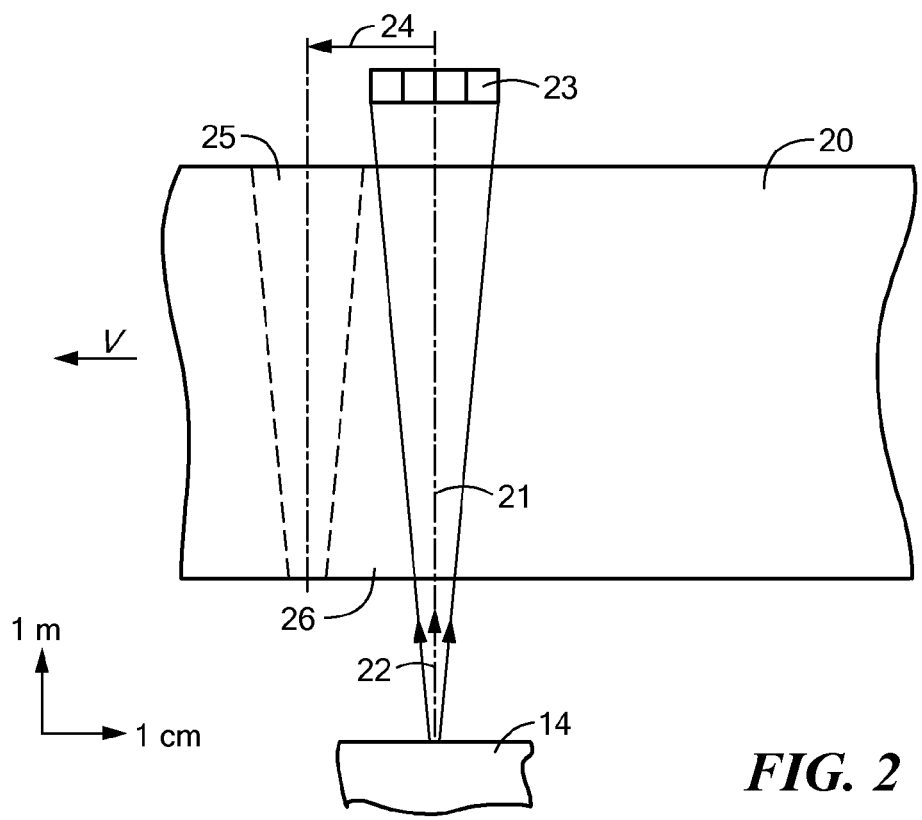
FIG. 2 is a horizontal plane cross-sectional schematic of cargo under inspection using a single beam and a two-dimensional detector array, viewed in the rest frame of the cargo.

One approach to x-ray cargo inspection that employs a single source and multiple detector arrays creates a single wide fan beam which covers a detector array N-pixels wide. Such a system, where, by way of example, N=4, is depicted in FIG. 2. The embodiment of FIG. 2 is not preferred, however, for reasons that will be discussed. The schematic cross-section shown in FIG. 2 is depicted in the frame of reference of cargo 20, which may be a container, or a truck, etc. X-ray beam 22 emerges from a collimator which constitutes part of source 14 of x-ray radiation. X-ray beam 22 traverses cargo 20, thereby interrogating an intervening segment 21 of the contents of cargo 20. Assuming that source 14 is pulsed, N=4 line images are obtained during each pulse from the incidence of beam 22 on detectors 23, which represent a section, in the plane of the page, of linear detector arrays extending up and down in a plane transverse to the plane of the page.

During the temporal interval between successive pulses, cargo 20 is displaced by distance 24, such that during the succeeding pulse, segment 25 of the cargo 20 is interrogated. It should be noted that, in accordance with this scheme, due to the quiescent interval between pulses, a region 26 fails to be interrogated at all.

Several deficiencies may detract from the approach depicted in FIG. 2, including the five deficiencies enumerated here:

1. The four image lines are projections with slightly different angles which leads to distortions unless the source is very far away;
2. There is very little space for the required photodetectors in a 2D array;
3. At the required high X-ray energies there is significant cross talk between neighboring scintillator crystals, as discussed, for example, by Descalle, et al., in "Detector design for high-resolution MeV photon imaging of cargo containers using spectral information," *Nucl. Instruments and Methods in Phys. Res. A*, vol. 624, pp. 635-40 (2010), incorporated herein by reference;
4. The wide beam 22 will result in increased scatter contributions relative to a narrow fan beam.
5. Some volume 26 of cargo will be not interrogated.

Figure 3:
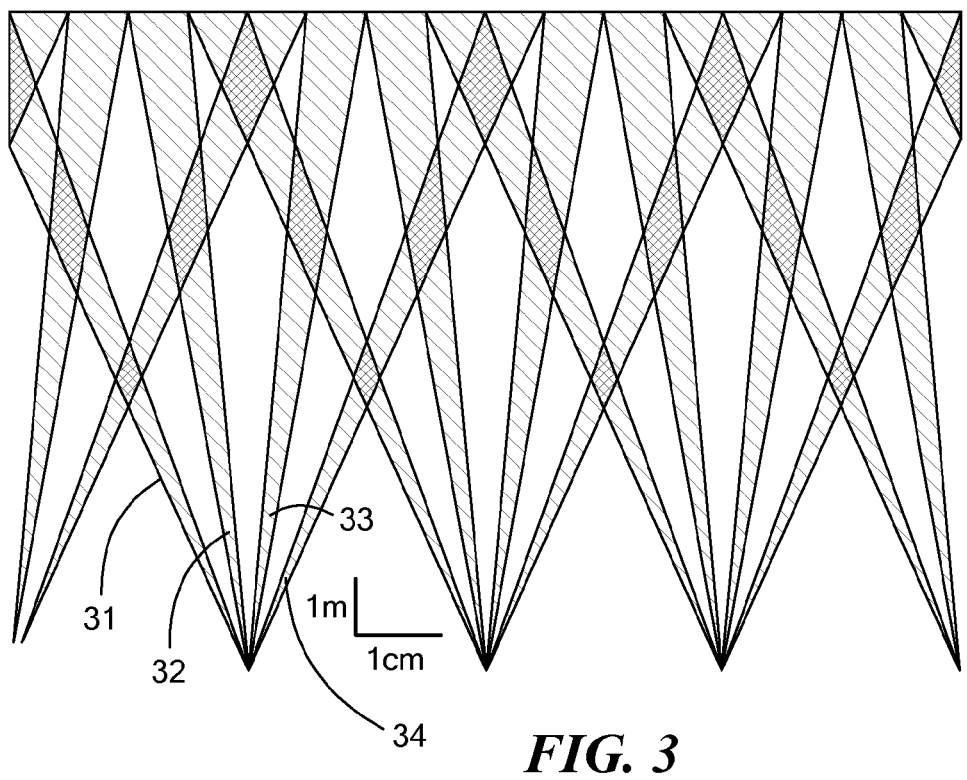
FIG. 3 is a schematic depiction of inspection by means of quadruple beams per source.

The deficiencies numbered 2 through 4 above can be avoided by creating multiple narrow fan beams from a single source. In that embodiment, each fan beam remains paired with a separate detector array. However, the approach of multiple narrow beams aggravates item 1 above. Now that the angle between the beam planes is even larger and discontinuous, overlapping projections are created. FIG. 3 illustrates the foregoing problem for a source with quadruple fan beams 31, 32, 33, and 34 per source. (Note that the aspect ratio is on the order of 100:1).

Creating Parallel Fan Beams

A solution preferable to that of FIG. 3 for very high speed imaging, and a solution which addresses all of the five previously enumerated issues, is that of employing a plurality of substantially parallel fan beams created by a single accelerator. In accordance with embodiments of the present invention, an accelerator is provided having multiple targets for one electron beam. Each target creates a source of Bremsstrahlung so that parallel fan beams can be created with a multi-slit parallel collimator.

Figure 4:
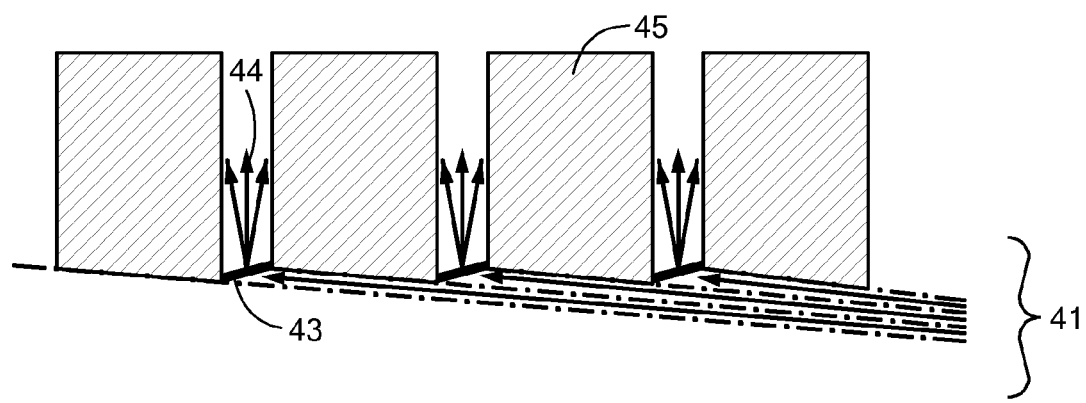
FIG. 4 shows extraction of multiple parallel fan beams transverse to an incident electron beam, in accordance with an embodiment of the present invention.

One such embodiment is now described with reference to in FIG. 4. Electron beam 41 is incident upon successive targets 43, and Bremstrahlung radiation 44 emitted substantially transverse to electron beam 41 is collimated by parallel collimators 45 into substantially parallel fan beams. It is to be noted that, for a 9 MeV electron beam 41 impinging on a thin target 43, the X-ray flux (per unit solid angle, $dI/d\Omega(\theta)$) 44 near 90° is only approximately 6% of the forward (0°) flux. For a 6 MeV electron beam that value is approximately 7%. Since only a small fraction of the total generated flux is utilized and is shared among multiple X-ray beams, a relatively large source current is required for the illustrated approach.

Figure 5:
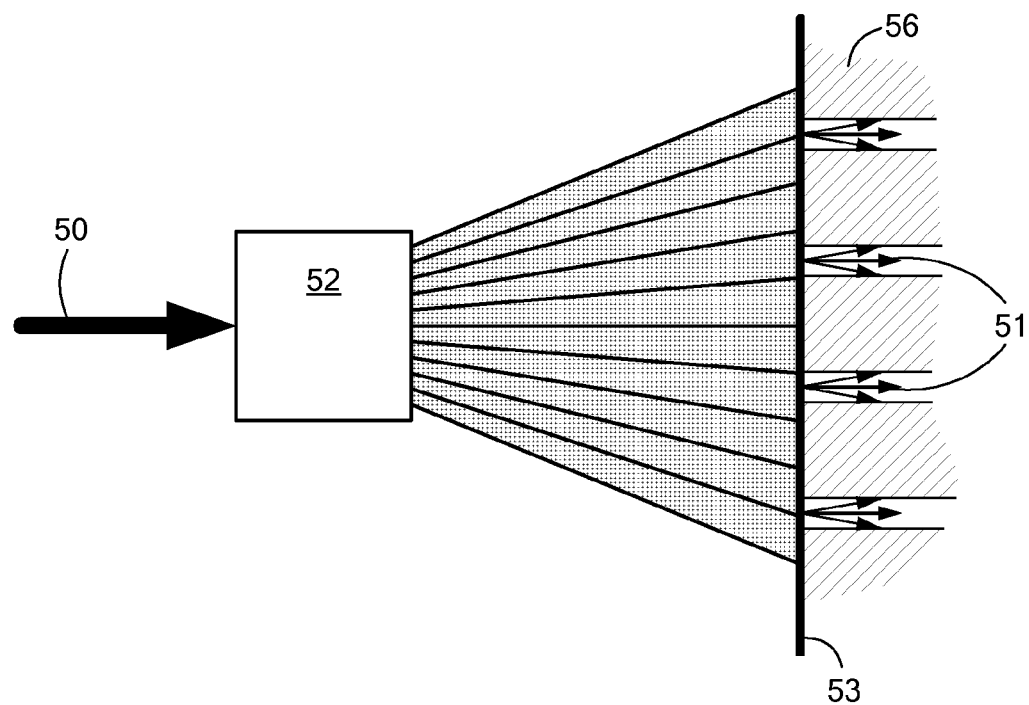
FIG. 5 is a cross-sectional schematic view of an apparatus for generating multiple parallel fan beams in planes to which the incident electron beam is parallel, in accordance with an embodiment of the present invention.

In an alternative embodiment of the present invention, described with reference to FIGS. 5 and 6, electron beam 50 is directed in line with (i.e., either within, or parallel to) the X-ray beam planes (the planes containing fan beams 51). Electron beam 50 is fanned out in the plane of the page by beam expander 52 so as to cover multiple targets 53. Any of the well-known techniques of control and expansion of charged particle beams by electromagnetic fields, or those yet to be developed, are within the scope of the present invention. If, as in the case shown in FIG. 5, no further beam optics are applied, only a fraction of the electron flux is utilized for generating the X-ray beams. However, since electron beam and X-ray beam differ only by a small angle, the strong forward lobe of the angular Bremsstrahlung distribution is used efficiently. Fan beams 51 emerging from respective targets are separately collimated by parallel collimator 56. Thus, the forward directed Bremsstrahlung of FIGS. 5 and 6 is more efficient than the transverse emission embodiment of FIG. 4.

Figure 6:
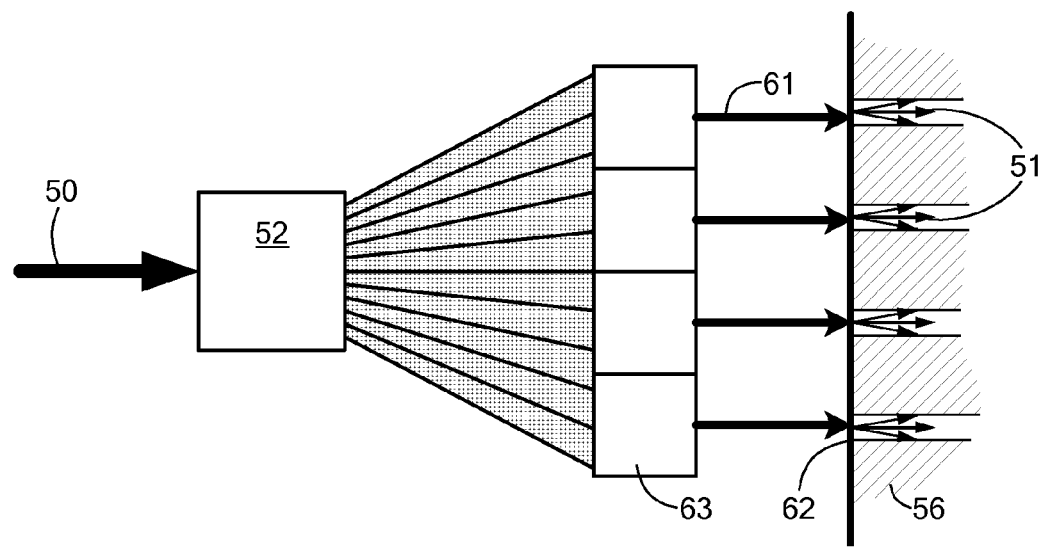
FIG. 6 is a cross-sectional schematic view of another apparatus for generating multiple parallel fan beams in planes to which the incident electron beam is parallel, in accordance with an embodiment of the present invention.

A significantly higher utilization of the electron flux can be achieved by separating the fanned out electron beam into multiple finger beams 61, each focused by beam focuser 63 to impinge upon its designated target 62 as shown in FIG. 6.

Another embodiment, for distributing the original electron beam 50 over multiple targets 53 employs switching, that is, redirecting the entire electron beam 50 onto one target 62 at a time.

Figure 7:
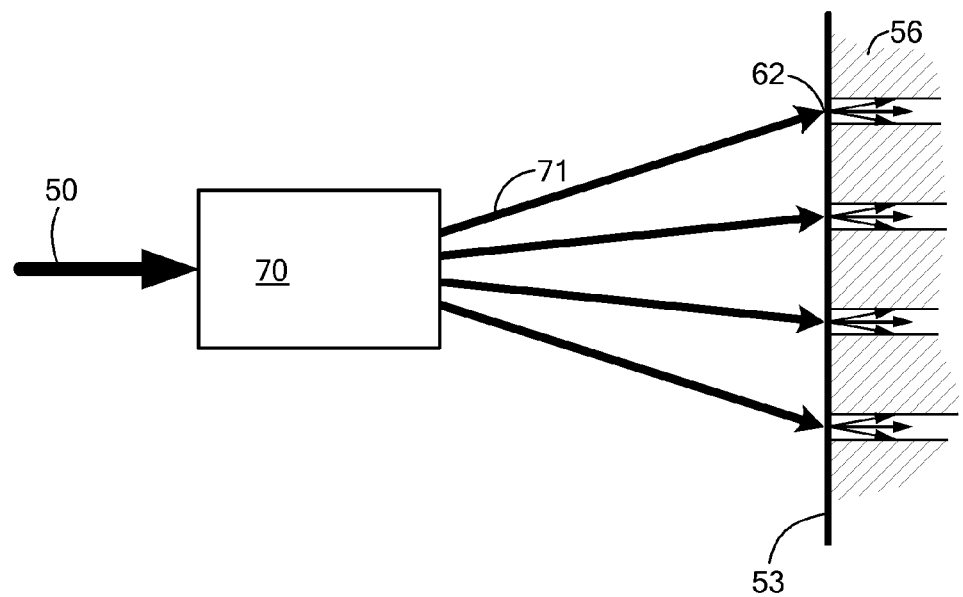
FIG. 7 is a cross-sectional schematic view of another apparatus for generating multiple parallel fan beams from multiple targets to the incident electron beam is switched in succession during the course of a single pulse, in accordance with an embodiment of the present invention.

U.S. Pat. No. 6,009,146, to Adler et al., describes moving an electron beam magnetically between multiple targets with stationary collimators to sequentially create multiple pencil beams of X-rays. The term "concurrent X-ray beams," as used herein and in any appended claims, refers to beams that exist within a time scale defined by the duration of a source pulse. To create multiple "concurrent" X-ray beams, within the foregoing meaning, a charged particle beam is switched by fast beam switcher 70, at a rate significantly higher than the pulse rate, as shown in FIG. 7. The target 62 for the electron beam 71, is thus also switched at a rate significantly higher than the pulse rate such that the electron beam is redirected many times during the duration of a single X-ray pulse, which typically lasts several microseconds. Beam-steering switchers (or "kickers") that operate on nanosecond time scales have been developed, and are described, for example, in the following publications, all incorporated herein by reference:

Lambertson, "*Dynamic Devices—Pickups and Kickers,*" in Physics of Accelerators, (eds. M. Month and M. Dienes), AIP Conference Proceedings 153, p. 1414 (1987);

Goldberg, et al., "*Dynamic Devices: A Primer on Pickups and Kickers*", in The Physics of particle Accelerators, eds. M. Month and M. Dienes, AIP Conference Proceedings 249, v. 1, p. 537 (1990);

Krasnykh, "*Development of a Fast High-Power Pulser and ILC DR Injection/Extraction Kicker*", SLAC-WP-077, presented at ILC Damping Ring R&D Workshop, Sep. 26, 2007-Sep. 28, 2007, Cornell University, Ithaca, N.Y. (2007); and Akre, et al., "*A Solid-State Nanosecond Beam Kicker Modulator, Based on the DSRD Switch*". SLAC-PUB-14418. Particle Accelerator Conference, (PAC'2011), New York, 2011;

Poole et al., "*Analysis and Modeling of a Stripline Beam Kicker and Septum,*" International Linear Accelerator Conference, Chicago, Ill., Aug. 23-28, 1998.

The fast beam switcher (kicker) 70 directs the entire electron beam onto the individual targets at a very high rate. The electron beam in a linear accelerator is not a steady stream of electrons but consists of a series of so-called micro bunches. To ensure the best utilization of the electron beam, the fast beam switching should be timed so that the switching of targets occurs between micro bunches. This is facilitated by linking the fast beam switcher to the same GHz frequency which drives the accelerator.

Multi-Beam Interlacing Schemes

One objective of embodiments of the present invention is that of acquiring a transmission X-ray image with complete coverage by equidistant scan lines. Multiple parallel beam planes paired with detector lines will produce multiple scan lines at a time. In order for these scan lines to produce a complete image, the detector lines need to be arranged with specified spacings and the pulse rate of the X-ray source needs to correspond to the speed of the object.

Figure 8:
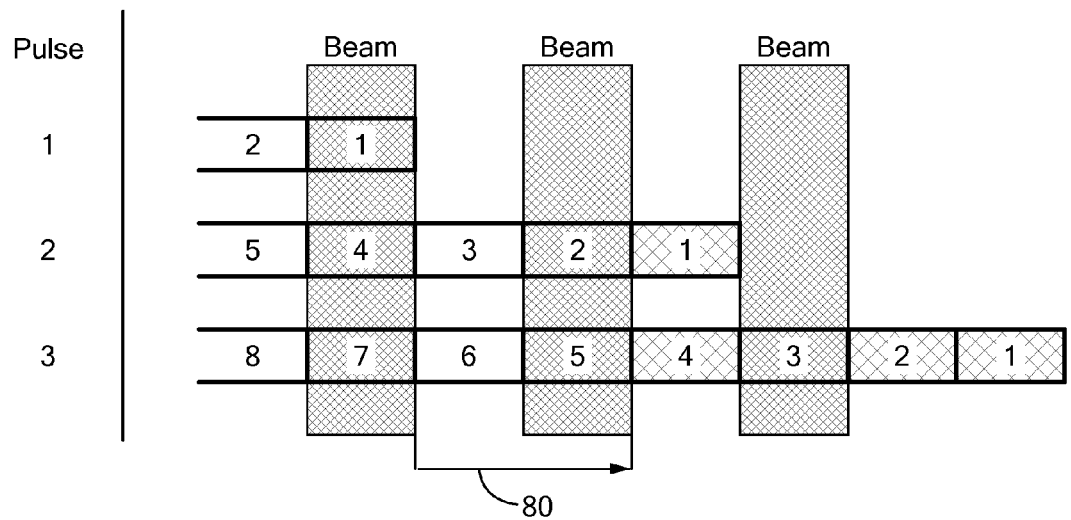
FIG. 8 depicts an interlacing scheme applicable to three parallel fan beams, where three detector arrays are spaced one beamwidth apart, in accordance with an embodiment of the present invention.
Figure 9:
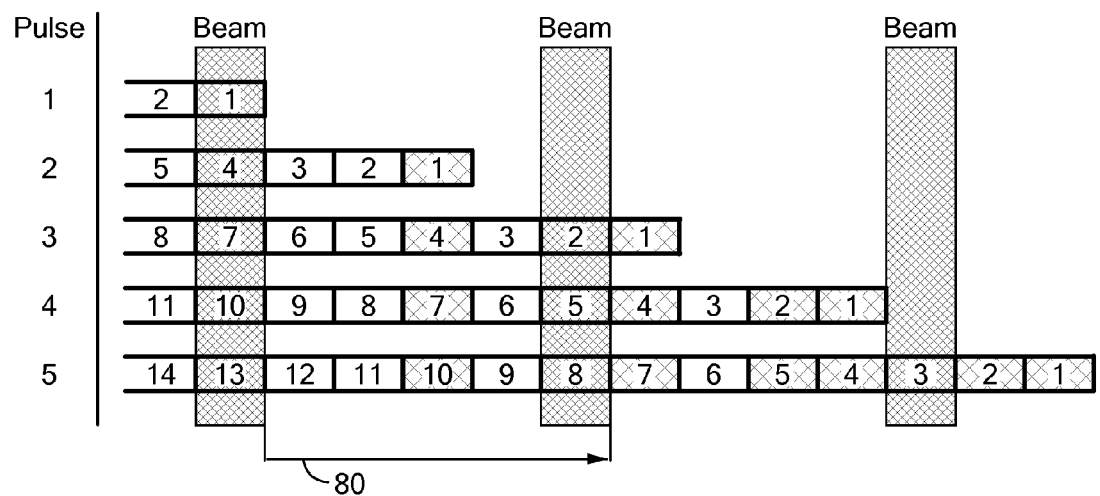
FIG. 9 depicts an interlacing scheme applicable to three parallel fan beams, where three detector arrays are spaced four beamwidths apart, in accordance with an embodiment of the present invention.

A multi-beam interlacing scheme in accordance with the foregoing considerations may be implemented with any number NB of fan beams, and the spacing of the detector lines depends on this number. For the case of three fan beams, for instance, the detector lines could be spaced one detector width DW apart or four DW apart. This is illustrated in FIG. 8 and FIG. 9, respectively. In these figures, time progresses from top to bottom, while the horizontal dimension represents space, with the motion of the inspected cargo designated by the numeral 80. Shading indicates that the respective cargo region has already been scanned.

In general, the minimum spacing between detector lines in units of DW is equal to NB−2, i.e., two fewer than the number of fan beams. The detector line spacing can be increased by multiples of the distance NB*DW.

The pulse rate in a multi-beam system is tuned to the speed of the imaged object (scan speed) in order to space the scan lines evenly over the imaged object.

$$\text{Pulse Rate} = \frac{\text{Scan Speed}}{NB * DW}$$

Equivalently, the maximum scan speed of the system is the product of the maximum pulse rate, the number of fan beams NB and the width of the detector DW:

Scan Speed=*NB*DW**Pulse Rate

So for instance a quad beam system with 1 cm wide detectors working at 400 pps allows scanning at 57.6 km/h. A quad beam system with 4 mm wide detectors needs to operate at 1000 pps for the same scanning speed.

Material Discrimination with a Multi-Beam System

Various approaches known in the art to acquire data which allow material discrimination are all compatible with the multi-beam concept.

Figure 10:
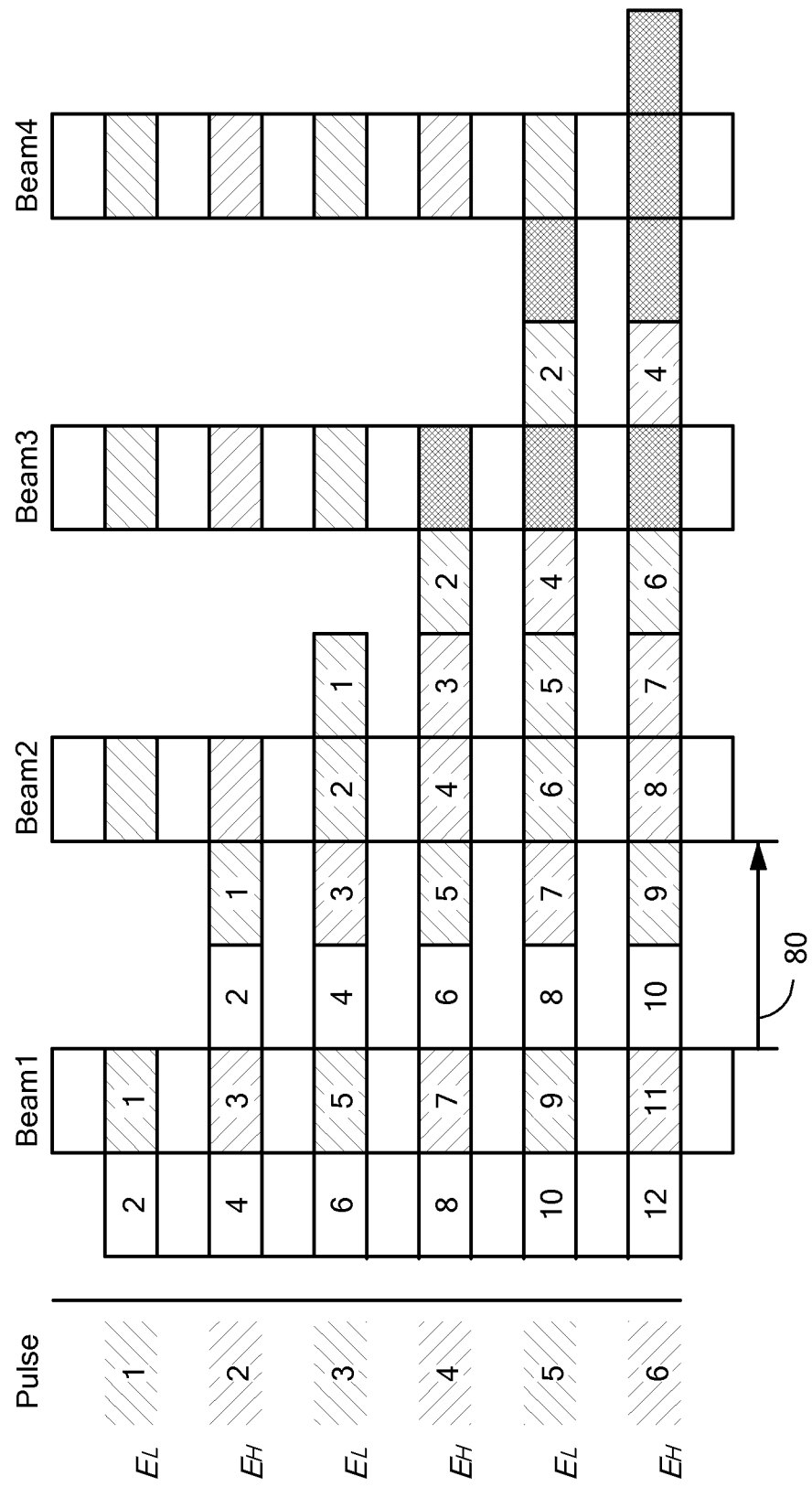
FIG. 10 depicts an interlacing scheme applicable to four parallel fan beams operating at two energies, where four detector arrays are spaced two beamwidths apart, in accordance with an embodiment of the present invention.

The most commonly applied dual energy method interlaces low and high end-point energy pulses in time. The image is composed by combining adjacent low and high energy pulses which effectively reduces the pulse rate by a factor two. A second disadvantage is that the low and the high energy scan lines being combined do not originate from exactly the same but neighboring regions in the scan object. Both these disadvantages can be addressed with the multibeam approach. If the source provides alternating low and high energy pulses and an even number of fan beams is used, simply scanning at a speed of Scan Speed=½NB*DW*Pulse Rate ensures that each cargo region will be scanned once with a low, and once with a high, end-point energy pulse. An example with four beams is shown in FIG. 10 where the two energies are represented by different hashing.

The other well established dual energy method uses detector elements which provide two differently filtered signals and thus enables material discrimination. This method is directly applicable with multiple beams.

The Scintillation-Cherenkov detector and method for high energy X-ray imaging disclosed in US Published Patent Application 2011/0163236 (Arodzero), incorporated herein by reference, and intrapulse multi-energy and adaptive multi-energy methods of cargo inspection disclosed in US Published Patent Application 2012/0093289 (Arodzero et al.), both incorporated herein by reference, are also directly applicable with the presently described multi-beam cargo inspection methods.

Further new methods are enabled with multiple beams, as the distinct beams may be filtered differently at the source. Alternatively, detector designs with differing energy sensitivities can be employed for different beams in the multibeam system.

Figure 11:
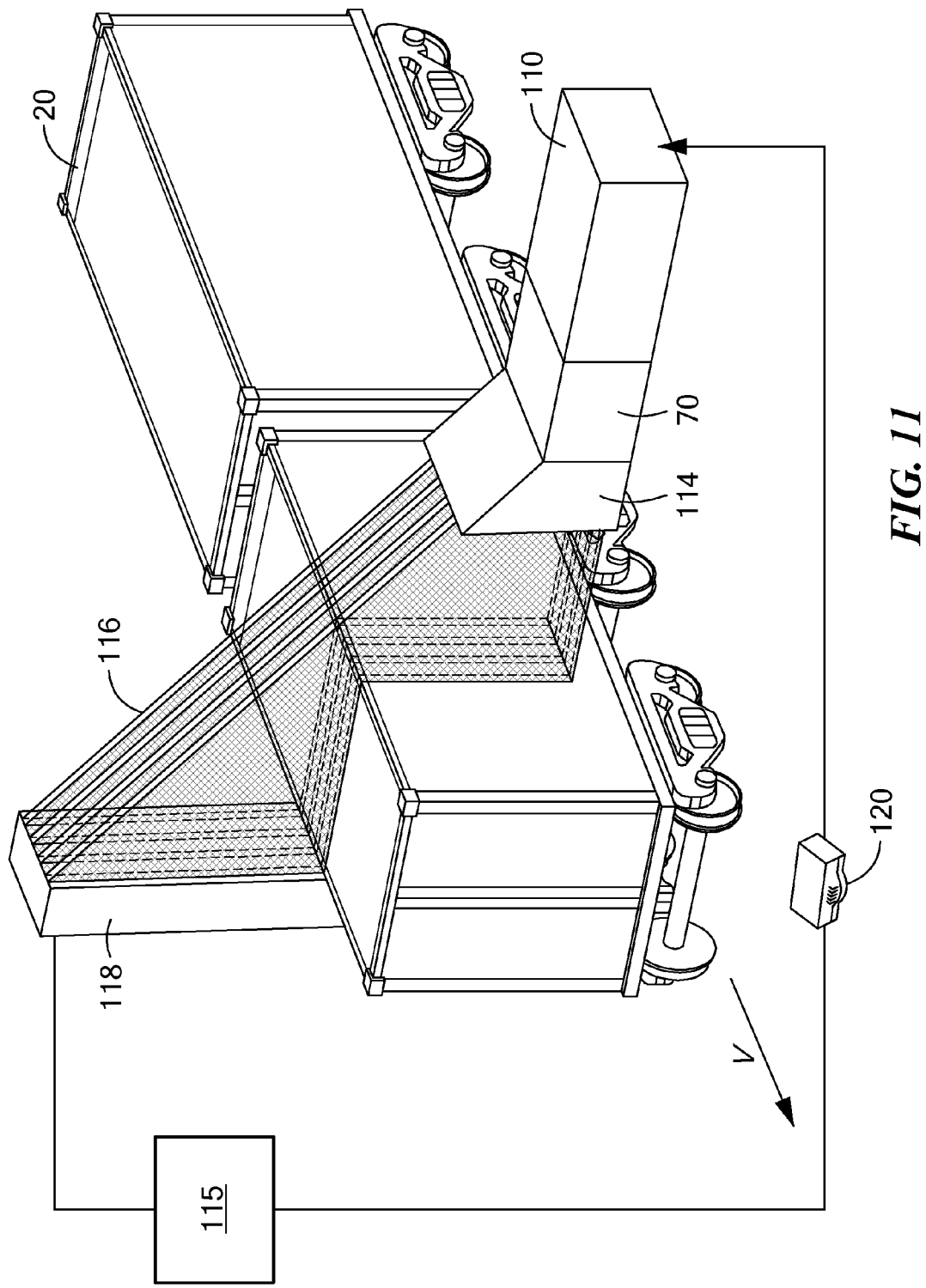
FIG. 11 shows a perspective view of a cargo inspection system in accordance with an embodiment of the present invention.

FIG. 11 shows a perspective view of a multi-beam cargo inspection system in accordance with an embodiment of the present invention. The electron beam of a linac-based X-ray generator 110 is switched by electron beam switcher 70 to multiple targets 62 (shown in FIG. 7) generating multiple beams 116 collimated by multi-slot collimator 114. Each beam corresponds to a linear array 118 of detectors on the opposing side of inspected cargo 20. A processor 115 receives detector signals from each detector module comprising the various linear detector arrays 118 and computes a relative transmission associated with each line of sight through the cargo 20. A speed sensor 120 may provide a signal to processor 115 for synchronizing cargo speed and source frequency to achieve specified resolution.

Where examples presented herein involve specific combinations of method acts or system elements, it should be understood that those acts and those elements may be combined in other ways to accomplish the same objective of providing a multiple x-ray fan beams from a single source. Additionally, single device features may fulfill the requirements of separately recited elements of a claim. The embodiments of the invention described herein are intended to be merely exemplary; variations and modifications will be apparent to those skilled in the art. All such variations and modifications are intended to be within the scope of the present invention as defined in any appended claims.

What is claimed is:

1. A cargo inspection system employing a plurality of concurrent fan beams of penetrating radiation, for inspecting cargo in motion relative to the cargo inspection system, the cargo inspection system comprising:
    a. a single source of a pulsed beam of accelerated electrons;
    b. a plurality of Bremsstrahlung targets for emitting penetrating radiation upon impingement by a spatial entirety of the pulsed beam during each of a plurality of pulses of the accelerated electrons;
    c. a plurality of collimators for forming the emitted penetrating radiation into a plurality of substantially parallel fan beams;
    d. a plurality of linear detector arrays, each linear detector array for receiving penetrating radiation transmitted through the cargo in a corresponding fan beam of the plurality of fan beams; and
    e. a processor for deriving a material characteristic of the cargo for each of a plurality of lines of sight through the cargo.

2. A cargo inspection system in accordance with claim 1, wherein an energy spectrum characterizing pulses of the penetrating radiation varies between distinct pulses as a function of time.

3. A cargo inspection system in accordance with claim 1, further comprising a speed sensor for providing a cargo speed to the processor.

4. A method for deriving a specified characteristic of an inspected object, the method comprising:
    a. generating, during a single pulse of accelerated electrons, a plurality of concurrent substantially parallel x-ray beams, by directing an entire electron beam onto a succession of Bremsstrahlung targets;
    b. concurrently irradiating the object with the plurality of concurrent substantially parallel fan beams of penetrating radiation;
    c. detecting the penetrating radiation after traversal of the inspected object with a plurality of linear detector arrays, thereby generating a detector signal; and
    d. processing the detector signal to derive the specified characteristic of the inspected object.

5. A method in accordance with claim 4, further comprising detecting each of the plurality of substantially parallel fan beams with a distinct detector array of the plurality of detector arrays in an interlaced manner.

6. A method in accordance with claim 4, wherein the penetrating radiation is generated in a plurality of pulses, each pulse characterized by an energy spectrum, and the plurality of pulses characterized by a pulse rate.

7. A method in accordance with claim 6 wherein the energy spectrum characterizing each of the plurality of pulses, varies from pulse to pulse, as a function of time.

8. A method in accordance with claim 7, further comprising interrogating a plurality of slices of the target with a plurality of pulses, wherein temporally adjacent pulses are characterized by distinct energy spectra.

9. A method in accordance with claim 6, further comprising synchronizing relative motion of the inspected object with the pulse rate.

* * * * *